(12) United States Patent
Moshinsky et al.

(10) Patent No.: US 8,795,253 B2
(45) Date of Patent: Aug. 5, 2014

(54) BI-DIRECTIONAL PERFUSION CANNULA

(75) Inventors: Randall Moshinsky, Malvern (AU); James McMillan, Parkdale (AU); Elli Tutungi, Glen Waverley (AU)

(73) Assignee: Sorin Group Italia S.r.l., Milan (IT)

( * ) Notice: Subject to any disclaimer, the term of this patent is extended or adjusted under 35 U.S.C. 154(b) by 274 days.

(21) Appl. No.: 13/418,473

(22) Filed: Mar. 13, 2012

(65) Prior Publication Data

US 2012/0259273 A1    Oct. 11, 2012

(30) Foreign Application Priority Data

Apr. 5, 2011   (AU) .................................. 2011901258
Jun. 3, 2011    (AU) .................................. 2011902210

(51) Int. Cl.
*A61M 25/00*    (2006.01)
*A61M 29/00*    (2006.01)

(52) U.S. Cl.
USPC .......................... 604/523; 604/524; 606/191

(58) Field of Classification Search
USPC .............. 604/164.01–170.01, 280, 523, 524; 606/191
See application file for complete search history.

(56) References Cited

U.S. PATENT DOCUMENTS

| | | | |
|---|---|---|---|
| 3,938,501 A * | 2/1976 | Erikson .......................... | 600/435 |
| 4,180,068 A | 12/1979 | Jacobsen et al. | |
| 4,790,315 A * | 12/1988 | Mueller et al. ................. | 606/194 |
| 4,895,564 A * | 1/1990 | Farrell ......................... | 604/164.1 |
| 4,994,027 A * | 2/1991 | Farrell ........................... | 604/510 |
| 5,171,218 A * | 12/1992 | Fonger et al. ............ | 604/164.02 |
| 5,190,528 A | 3/1993 | Fonger et al. | |
| 5,330,433 A | 7/1994 | Fonger et al. | |
| 5,354,276 A | 10/1994 | Fonger et al. | |
| 5,522,834 A | 6/1996 | Fonger et al. | |
| D408,529 S | 4/1999 | Hechel | |
| 5,928,192 A * | 7/1999 | Maahs ....................... | 604/96.01 |
| 5,980,503 A | 11/1999 | Chin | |
| 6,090,072 A * | 7/2000 | Kratoska et al. ......... | 604/164.01 |
| 6,186,981 B1 * | 2/2001 | Cho ............................. | 604/117 |
| 6,497,698 B1 | 12/2002 | Fonger et al. | |
| 6,645,193 B2 | 11/2003 | Mangosong | |

(Continued)

FOREIGN PATENT DOCUMENTS

| | | |
|---|---|---|
| WO | WO00/04942 | 2/2000 |
| WO | WO03/068303 | 8/2003 |
| WO | WO2005/037345 | 4/2005 |

OTHER PUBLICATIONS

Matsui et al.; "A Novel Femoral Arterial Cannula to Prevent Limb Ischemia During Cardiopulmonary Support: Preliminary Report of Experimental and Clinical Experiences"; from Artif Organs, vol. 30, No. 7, 2006; pp. 557-560.

(Continued)

*Primary Examiner* — Kevin C Sirmons
*Assistant Examiner* — William Carpenter
(74) *Attorney, Agent, or Firm* — Faegre Baker Daniels LLP

(57) ABSTRACT

A bi-directional perfusion cannula is provided that includes an elongate tube for insertion into an artery. The elongate tube has a first aperture at a distal end of the tube which is forward during insertion and configured so that blood can flow into the artery in the direction of insertion, an elbow formed in the elongate tube, and a second aperture formed in or slightly rearward of the elbow and configured for supplying blood into the artery in a second direction which is generally opposite to the insertion direction.

20 Claims, 6 Drawing Sheets

(56) References Cited

U.S. PATENT DOCUMENTS

| | | |
|---|---|---|
| 6,676,650 B1 * | 1/2004 | Magovern et al. ............ 604/508 |
| 6,689,149 B2 | 2/2004 | Maahs |
| 7,056,294 B2 | 6/2006 | Khairkhahan et al. |
| D533,270 S | 12/2006 | Kierce et al. |
| 7,267,660 B2 | 9/2007 | Fonger et al. |
| 2002/0022822 A1 * | 2/2002 | Cragg et al. ................. 604/500 |
| 2003/0216688 A1 | 11/2003 | M.A.J.M. et al. |
| 2008/0082080 A1 * | 4/2008 | Braga ........................... 604/523 |
| 2010/0312123 A1 * | 12/2010 | Phillips ........................ 600/485 |

OTHER PUBLICATIONS

Magovern et al., "A Femoral Artery Cannula That Allows Distal Blood Flow"; from The Journal of Thoracic and Cardiovascular Surgery, Sep. 2005; pp. 684-686.

* cited by examiner

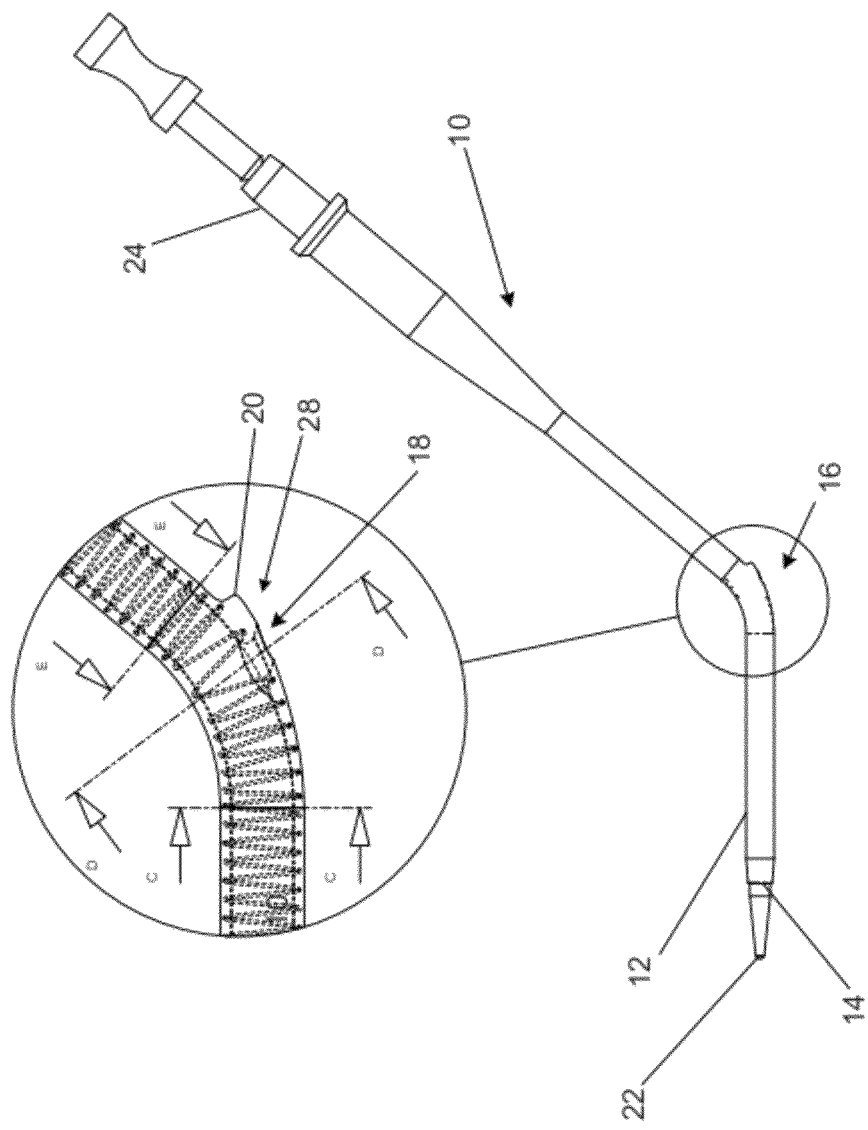
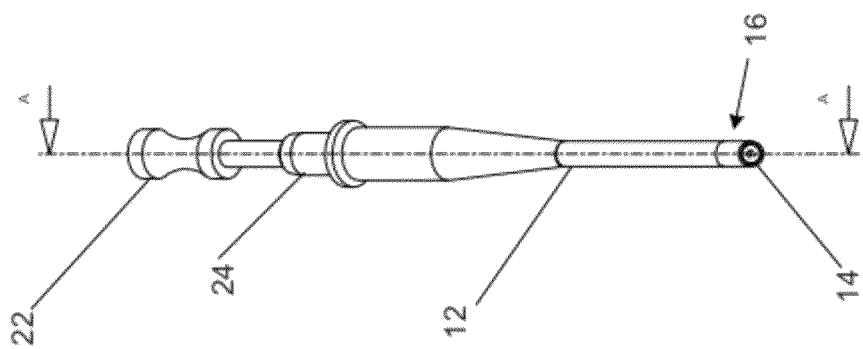

Section C-C

Section D-D

Section E-E

BI-DIRECTIONAL PERFUSION CANNULA

CROSS-REFERENCE TO RELATED APPLICATIONS

This application claims the benefit of Australian Patent Applications Nos. 2011901258, filed on Apr. 5, 2011; and 2011902210, filed on Jun. 3, 2011. The entire disclosures of each of the above applications are incorporated herein by reference.

FIELD

The present disclosure relates to a bi-directional perfusion cannula.

BACKGROUND

This section provides background information related to the present disclosure which is not necessarily prior art.

Some cardiac surgery procedures require peripheral artery cannulation for cardiopulmonary bypass. Also, some disease states require mechanical cardio-pulmonary support via peripheral artery cannulation. This peripheral artery is often, but not always, the femoral artery. Insertion into the femoral artery of an arterial cannula of sufficient size to support the patient with cardiopulmonary bypass often leads to compromised blood flow to the lower limb which can lead to ischemia and tissue necrosis during prolonged procedures.

Previously proposed methods of providing perfusion to the body while maintaining perfusion to the lower limb are generally inconvenient and often do not provide a satisfactory solution.

It has previously been proposed to use an undersized cannula, based on the assumption that the smaller cannula will allow blood flow back over the body of the cannula between the cannula body and the arterial wall. In practice it is difficult to achieve adequate perfusion to the lower limb and using a cannula of a smaller size than what is actually required compromises perfusion to the body and increases line pressures, thus increasing the risk of red blood cell haemolysis, increased backpressure to the membrane oxygenator and the perfusion pump and the increased risk of damage to these vital pieces of equipment.

It has also been previously proposed to insert a further perfusion cannula downstream of a first, main perfusion cannula. Inserting a downstream cannula can be technically difficult and a percutaneous approach often requires ultrasound guidance to allow accurate placement. This technique requires an extra cannula and an extra perfusion line that must be connected into the arterial side of the perfusion circuit and can be time consuming. It also results in extra hardware being disposed in the groin incision area, an area that is already compromised for space with the femoral arterial and femoral venous lines already in place. The downstream cannula would typically be a small cannula which is more susceptible to positional changes, resulting in less reliable downstream flow.

It has also been previously proposed to sew a side graft to the artery when using femoral artery cannulation. In this technique, surgeons sew on a Dacron graft to the side of the femoral artery as an end to side anastamosis and a cannula is inserted into the graft. This technique is time consuming, taking approximately 30 minutes to sew on the graft and cannulate it, compared with approximately 2 minutes to insert a bidirectional femoral cannula. Furthermore, this technique requires an open surgical procedure which can be difficult in an ICU setting. Bleeding can also be a problem in patients requiring extended periods of support and when support ceases, the base of the Dacron graft may be left in situ with this technique, creating a potential source for thrombus formation and infection.

It is desirable to provide a single cannula that provides adequate perfusion to the lower limb. However, as will be discussed below, previously proposed cannulae suffer a number of drawbacks.

It has been previously proposed to provide a conventional cannula with side perfusion holes through which blood can flow toward the lower limb. Such arrangements have been disclosed in WO03/068303 to Laksen et al. and in "A Novel Femoral Arterial Cannula to Prevent Limb Ischemia During Cardiopulmonary Support Preliminary Report of Experimental and Clinical Experiences" by Matsui et al. in *Artif Organs*, Vol. 30, No. 7 2006. In arrangements having side perfusion holes, the cannula must be correctly positioned in the artery so that the holes are not occluded, and maintained in that position. In these arrangements, no tactile feedback is available to assist with positioning of the holes and assistance in maintaining the holes in correct position is not provided. If the cannula migrates distally the holes will be occluded by wall of artery. If the cannula migrates proximally then the holes may move outside of the artery and cause bleeding. If the side holes are at level of the arteriotomy, perfusion into the wall of the artery may cause a dissection.

To prevent occlusion of side holes provided in a conventional cannula, it has been proposed to provide rails adjacent the holes to prevent occlusion of the holes. Such an arrangement has been disclosed in "A femoral artery cannula that allows distal blood flow" by Magovem, J. et al. (*The Journal of Thoracic and Cardiovascular Surgery, September* 2005). The configuration of the rails can be complicated and difficulties will be encountered with their insertion and removal through the wall of the artery. The rails also create a ridged cross section which creates a potential for bleeding during insertion and removal. Furthermore, blood passing through the side holes is not efficiently communicated as it is directed against the wall of artery.

Alternative rail configurations have also been proposed to facilitate insertion of the cannula into the artery while attempting to prevent occlusion of side holes. Documents U.S. Pat. No. 5,171,218 and U.S. Pat. No. 5,330,433 by Fonger, J. et al, each disclose an arrangement in which the rails are in the form of forward pointing barbs between which a slanted elongate hole located in a depression on the exterior of the wall of the cannula is disposed. The depression impinges into the main lumen to act as a scoop to divert blood toward the lower limb.

As with previous proposals, difficulties will be encountered with insertion and removal due to the cross sectional shape of the barbs, which, as can be seen in FIG. 5 of each of the documents, is ridged in the region of the barbs/rails and will require the artery to stretch during insertion and removal. As this region passes through the artery wall, this ridged cross section may also create channels between the ridges that may result in bleeding during insertion and removal.

Furthermore, the main lumen is narrowed by the side hole depression, thereby reducing flow capability. The most important determinant of flow through a cannula, as determined by the Poiseulle-Hagen equation, is cannula radius. Decreasing radius by half causes a decrease in flow of sixteen times. Reducing the radius in a femoral cannula that is already being pushed to achieve maximal flow rates is a major compromise in the primary function, that is, providing flow equal to systemic cardiac output.

Due to the configuration of the barbs and the side aperture, this arrangement may be difficult to manufacture. Furthermore, flow from the side aperture does not have an open area of artery to flow into, thereby reducing flow efficiency and creating an area of turbulent flow.

As discussed above, each of the previously proposed bi-directional cannulae have suffered from a number of problems. Furthermore, general poor performance has been observed due to issues with occlusion of side facing holes/apertures. The Inventors have found that the previous poor performance can at least partially be attributed to two factors, arterial spasm and downstream compression.

Arterial Spasm relates to the normal physiological response of contraction of arterial smooth muscle to stretch or local trauma. Arterial spasm around the body of the cannula will result in a reduction of blood flow back around the cannula and down the leg. This can even occur around undersized cannula.

Downstream Compression, as illustrated in FIG. 1, is a mechanism that has not been previously acknowledged. The body of a standard femoral cannula causes a distortion of the arterial wall around the point of insertion. As the cannula tends to lie in the orientation of the artery, the body of the cannula causes a downward displacement of the distal edge of the arteriotomy, and compression of the artery just distal to the arteriotomy. Obstruction of flow downstream to the arteriotomy has to be overcome if reliable downstream flow is to be provided.

The issues of arterial spasm and downstream compression have not been acknowledged or addressed in the previous proposals.

Examples of the invention seek to solve, or at least ameliorate, one or more disadvantages of previous cannulae.

SUMMARY

This section provides a general summary of the disclosure, and is not a comprehensive disclosure of its full scope or all of its features.

According to the present invention, there is provided a bi-directional perfusion cannula comprising an elongate tube for insertion into an artery, the elongate tube comprising: a first aperture at a distal end of the tube which is forward during insertion, the first aperture being configured so that blood can flow into the artery in the direction of insertion; an elbow formed in the elongate tube; and a second aperture, the second aperture being formed in or slightly rearward of the elbow and configured for supplying blood into the artery in a second direction which is generally opposite to the insertion direction.

Preferably, the elbow is preformed in the elongate tube such that in a relaxed state prior to insertion the cannula has an elbow bend formed in it, preferably in the range of 90 to 180 degrees.

Preferably, the elongate tube has a protuberance at least partially formed on the elbow, the protuberance being configured to facilitate positioning of the cannula in the artery. Preferably, the protuberance and elbow form a transition zone which splints open the artery. In one embodiment, the transition zone is inflatable. Preferably, the protuberance can taper in the insertion direction to allow insertion of the cannula in the artery.

Preferably, a rearward portion of the protuberance tapers at a greater rate than it does in the insertion direction so as to provide greater resistance during removal than during insertion.

A side profile of the protuberance can have the form of a shoulder, preferably a rounded shoulder.

The protuberance can be generally ovoid in cross section. The protuberance can extend generally along an outer surface of the elbow. Preferably, the second aperture extends through the protuberance. Preferably, the second aperture extends in a direction generally away from the forward end of the tube.

The elongate tube can terminate at the first aperture. The elongate tube can be configured to receive an elongate introducer therethrough to aid in insertion of the cannula and prevent blood flow through the first aperture whilst the elongate tube and introducer are inserted into an artery.

The elongate tube can be configured so that an internal diameter of the elongate tube, in a region around the second aperture, is greater than a diameter of a corresponding portion of the elongate introducer when received therethrough so that blood can pass into the elongate tube through the second aperture to indicate that the second aperture has passed into the artery. Preferably, the internal diameter of the elongate tube is generally constant along a length of the tube.

Preferably, the elbow bends through an angle of approximately 130 degrees. The elongate tube can be formed of flexible material so as to at least partially straighten when an introducer is inserted into the cannula. The elongate tube can be formed of a wire-reinforced flexible polyurethane material.

Preferably, the cannula is configured to be inserted into a femoral artery. The cannula can also be configured to be inserted into a subclavian or axillary artery.

The cannula can further include a manometer tube in communication with a pressure transducer, the manometer tube configured for measuring the pressure of blood flowing in the second direction.

According to the present invention, there is also provided, in combination, a bi-directional perfusion cannula of the above described type and a tapered introducer received through the elongate tube.

According to another aspect of the present disclosure, a bi-directional perfusion cannula comprises an elongate tube configured for insertion into an artery. The elongate tube includes a distal portion, a proximal portion and an intermediate portion. The distal portion comprises a generally cylindrical shape extending along a first longitudinal axis, a generally circular cross-section having a substantially uniform wall thickness, and a first aperture operable to direct blood flow from the tube in a first direction. The proximal portion comprises a generally cylindrical shape extending along a second longitudinal axis that is not collinear with the first longitudinal axis, and a generally circular cross-section having a substantially uniform wall thickness. The intermediate portion extends between the distal portion and the proximal portion and comprises a generally arcuate shape and a generally oval cross-section comprising a substantially non-uniform wall thickness, and a portion of the wall having a greater wall thickness comprises a shoulder tapering outwardly in the direction toward the proximal portion. A passageway comprising a substantially unobstructed flow path passes through the intermediate portion and a second aperture operable to direct blood flow from the tube in a second direction that is generally opposite to the first direction is also included and comprises an opening from the passageway through the portion of the wall having a greater wall thickness.

In another aspect of the present disclosure, the shoulder has a length that approximates the distance between the interior walls of the artery and which facilitates stenting open the artery at a downstream side of the point of insertion of the tube.

In still another aspect of the present disclosure, the intermediate portion bi-directional perfusion cannula comprises means for alleviating compression of the artery into which the cannula is inserted in a portion of the artery located downstream of the point of insertion of the cannula, means for stenting open the artery into which the cannula is inserted at a downstream side of the point of insertion of the cannula, and means for directing blood flow from the cannula in a downstream direction.

According to the present invention, there is also provided a method of inserting into an artery a bi-directional perfusion cannula comprising an elongate tube having a first aperture at a distal end for supplying blood into the artery in a direction of insertion, an elbow formed in the elongate tube, a protuberance formed at least partially on the elbow and a second aperture formed in the protuberance for supplying blood into the artery away from the insertion direction, the method comprising the steps of: feeding the distal end of the elongate tube into the artery until an increase in resistance to insertion is felt to indicate that the protuberance is entering the artery; easing the elongate tube into the artery until the elbow and the protuberance have passed into the artery and the amount of resistance reduces; and retracting the elongate tube until an increase in resistance to retraction is felt to indicate that the protuberance is abutting the artery wall and the cannula is in position.

Preferably, blood flows into the elongate tube through the second aperture after the second aperture has been eased into the artery.

Preferably, after treatment the cannula is retracted by easing the protuberance through a wall of the artery, whereby an opening formed in the artery wall is gradually enlarged by the increasing cross sectional size of the protuberance so that the elongate tube can be removed generally without causing further trauma to the artery.

According to the present invention, there is also provided a method of providing perfusion to a limb during peripheral artery cannulation, the method including the steps of: inserting a cannula of the above described type into an artery; pumping blood through the cannula to the artery; and monitoring the pressure measured by the pressure transducer to ensure that an adequate level of blood flow to the limb is provided.

According to preferred embodiments, the pressure of blood flowing in the second direction is constantly monitored and maintained in a range which is close to a pressure level in the second direction determined at the commencement of flow.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

The invention will be further described, by way of non-limiting example only, with reference to the accompanying drawings in which:

FIG. 4 is a front view of the cannula with wire reinforcement removed for clarity;

FIG. 5 is a side view of the bi-directional perfusion cannula of FIG. 4;

Corresponding reference numerals indicate corresponding parts throughout the several views of the drawings.

DETAILED DESCRIPTION

Example embodiments will now be described more fully with reference to the accompanying drawings.

Figure 2:
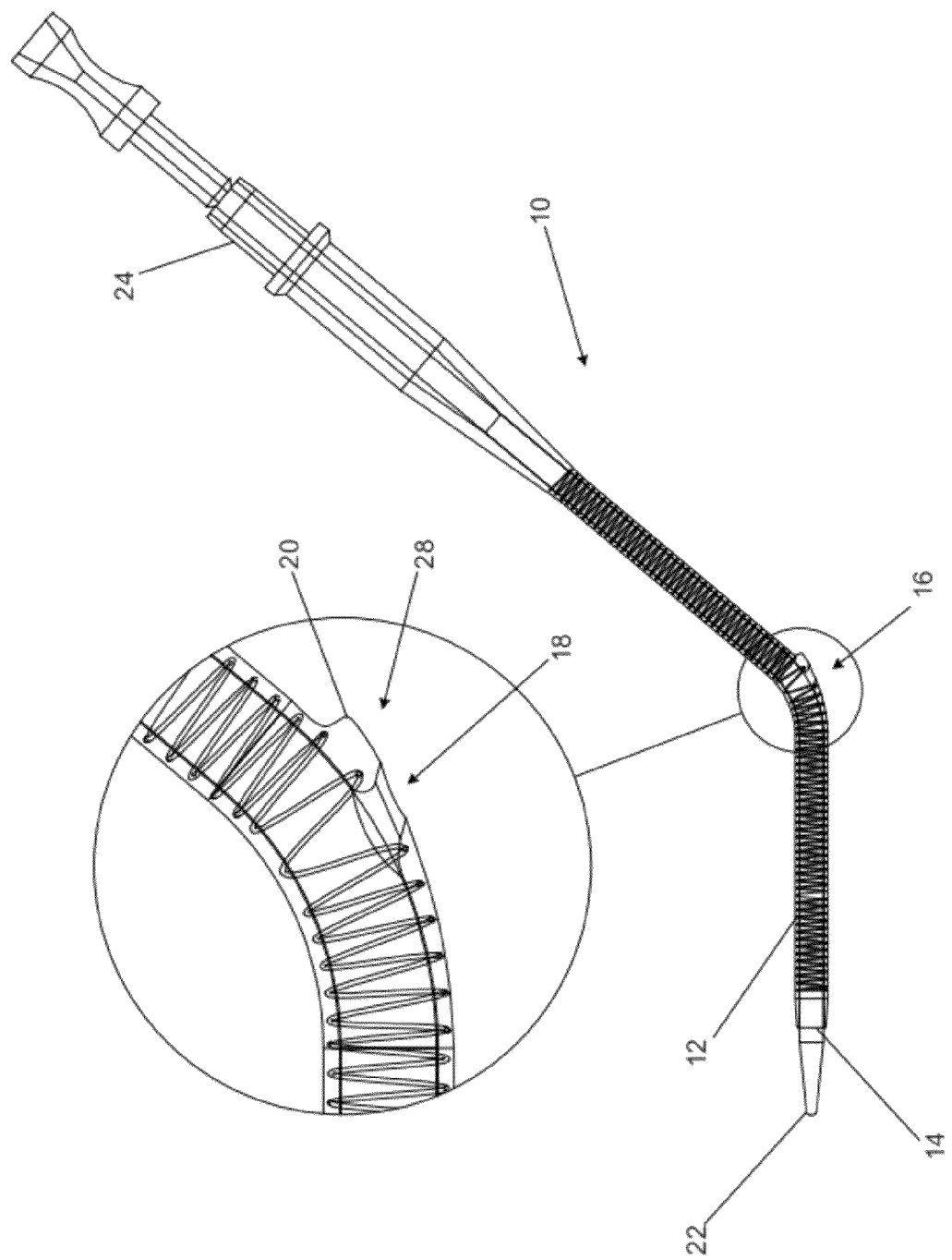
FIG. 2 is a side view of a bi-directional perfusion cannula of one embodiment of the invention, with an introducer received therein.

With reference to FIG. 2, there is shown a bi-directional perfusion cannula 10 comprising an elongate tube 12 configured for insertion into an artery. The elongate tube 12 comprises a first aperture 14 at a distal end of the elongate tube 12 which is forward during insertion of the cannula into an artery. The first aperture 14 is configured so that blood can flow into the artery in the direction of insertion and towards the arterial circulation of the patient.

The elongate tube 12 also comprises an elbow 16 which is formed in the elongate tube. The elbow 16 is preformed such that in a relaxed state prior to insertion the cannula has an elbow bend in it. In the example shown, the elbow bends through an angle of 130 degrees, which has been found to be the angle that best alleviates the downstream compression of the artery distal to the arteriotomy and allows the cannula to achieve a suitable lie outside the artery. It will be appreciated that other angles, such as 120 degrees, and particularly those in the range of 90 to 180 degrees may also be suitable. Angles outside of this range may not be effective at alleviating downstream compression or allowing the intravascular and extra vascular sections of the cannula to achieve a suitable lie. The elbow 16 allows the elongate tube 12 to transition a suitable amount so that a second aperture 18, in the form of a rearward facing aperture can be provided for bi-directional perfusion.

Figure 1:
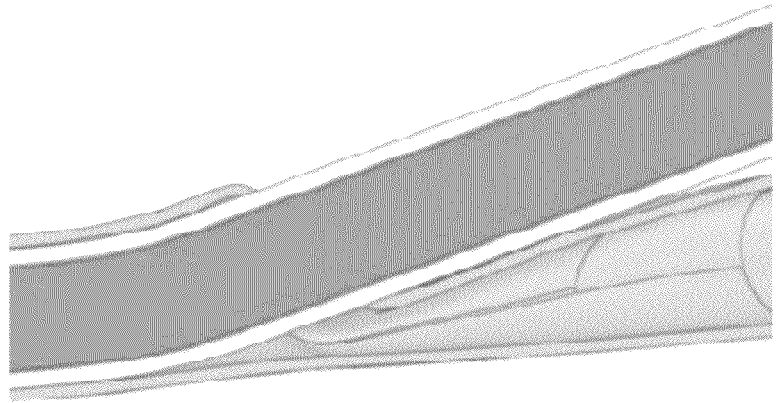
FIG. 1 is a sectional side view of a conventional cannula inserted into an artery.
Figure 7:
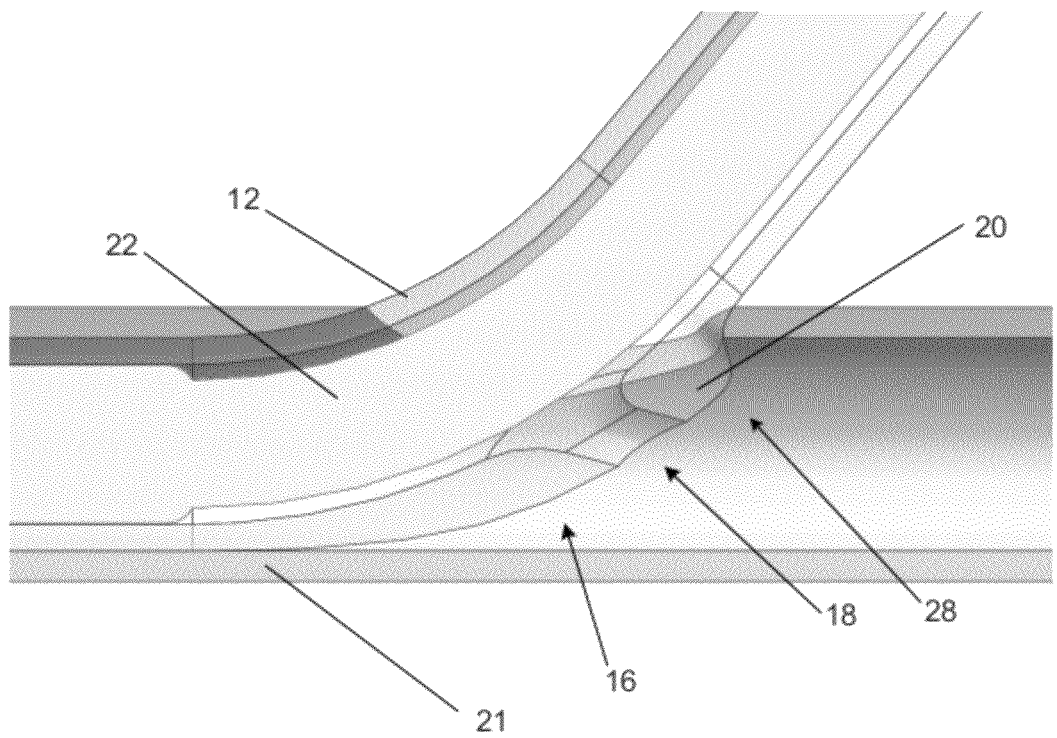
FIG. 7 is a sectional view of the cannula inserted into an artery.

Previously proposed arrangements, such as those disclosed in Fonger et al, do not include an elbow so that a rearward facing aperture directing blood into the artery and not into the artery wall can be provided. The inventors have found that, in use, an artery which is naturally flexible, and less rigid than a conventional cannula, tends to bend around a straight cannula when inserted in the artery, thereby acting to close the artery in the manner shown in FIG. 1. Arrangements having side facing holes are particularly susceptible to this problem. By providing an elbow and a rearward facing aperture, it is possible to avoid obstruction or covering of the aperture by the artery wall, as illustrated in FIG. 7, thus increasing the effectiveness of the cannula. In particular, the problems discussed above in relation to arterial spasm and downstream compression can be alleviated as the rearward facing aperture is away from the artery wall.

The elbow 16 also assists in positioning of the cannula 10 as it passes from the femoral artery to the surface of the leg.

The angle used for the elbow 16 is selected so as to reduce the amount of downstream or distal artery compression.

As illustrated, the second aperture 18 is formed in or slightly rearward, i.e. away from the insertion or forward direction, of the elbow 16. The second aperture 18 faces rearward and is configured for supplying blood into the artery in a second direction which is generally opposite to the forward or insertion direction so as to achieve bi-directional perfusion in the artery. In the examples shown, the second aperture 18 is formed in the elbow, though it may be formed slightly rearward of the elbow and still provide adequate bi-directional perfusion in the artery. Forming the second aperture 18 in or slightly rearward of the elbow 16 allows a second path for blood flow to be provided without impinging on or narrowing the lumen of the elongate tube 12, thereby avoiding a reduction in blood flow through the cannula 10. The configuration of the elbow 16 and the second aperture 18 is such that when the cannula 10 is inserted into the artery, the second aperture 18 is correctly orientated within the artery.

Figure 6A:
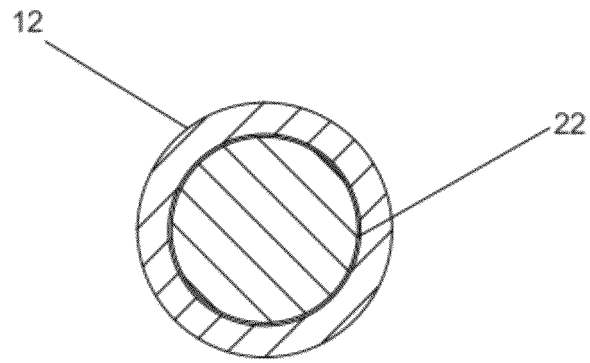
FIGS. 6A, 6B and 6C are sectional views of the cannula of FIG. 5, the sections being taken along lines C-C, D-D and E-E of FIG. 5 respectively.
Figure 6B:
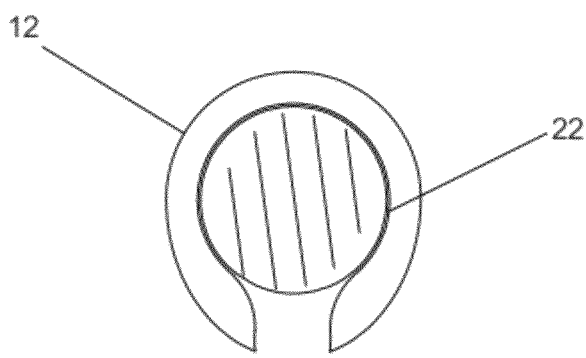
Figure 6C:
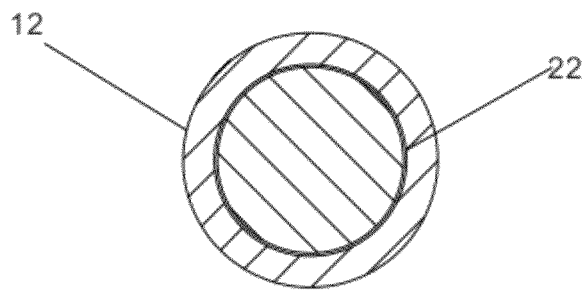

The elongate tube 12 has a protuberance 20 which is formed on the elbow 16 and is configured to facilitate insertion and positioning of the cannula 10 in the artery. The protuberance 20 is formed on and extends along an outer surface of the elbow 16. As can be seen in FIGS. 6A to 6C, the extent of the protuberance 20 is generally limited to a lower one half of the cross section and is not visible when viewed from in-front (FIG. 4) or above the cannula 10.

The protuberance 20 tapers in the insertion direction to allow insertion of the cannula into the artery with minimal trauma. In this regard, the taper is gradual so as to allow the artery wall to gradually expand as the cannula 10 is inserted. The angle of the taper is between approximately 3 to 25 degrees. For differently sized cannulae, the taper angle will be the same, though the maximum thickness of the protuberance will depend on the size of the cannula. For example, a 20F cannula will have a protuberance with a maximum thickness, excluding the thickness of the elongate tube on which it is formed, of approximately 1.5 mm. It will be appreciated that the size of the protuberance formed on smaller cannulae will be scaled down and smaller.

The size of the protuberance 20 is small enough so as to allow insertion of the cannula 10 into the artery with minimal trauma, though large enough to prevent accidental dislodgement of the cannula 10. The size of the protuberance 20 is also sufficient so that the second aperture 18 can be positioned within the protuberance 20 so as to orientate the second aperture 18 within the artery.

An intermediate portion (see the enlarged detail of FIG. 2) comprises the protuberance 20 and elbow 16 which together form a transition zone 28 where a cross sectional size of the elongate tube 12 gradually increases and then decreases so that it can be inserted into the artery with minimal trauma inflicted on the artery wall. In the examples shown, the protuberance 20 is generally ovoid in cross section, as can be seen in FIGS. 6A, 6B and 6C, though other shapes may also be used.

The transition zone 28 acts to splint open the artery so that the artery is not compressed by the body of the cannula and allows unimpeded flow in the second direction. The transition zone 28 acts to support the artery wall away from the second aperture 18 so that the artery is held open and does not block the flow of blood from the cannula 10 into the artery. The transition zone 28 also acts to provide stability to the cannula 10 when inserted in an artery so as to maintain the cannula 10 in position.

A rearward portion of the protuberance 20 tapers at a greater rate than it does in the insertion direction so as to provide greater resistance during removal than during insertion. The rearward portion of the protuberance 20 tapers more sharply so that a side profile of the protuberance 20 generally has the form of a rounded shoulder.

The inventors have found that by providing a protuberance in the form of a rounded shoulder, a good balance between minimising arterial trauma during removal and resistance to removal can be achieved. The protuberance also provides a self-locating mechanism. In this regard, the increased resistance provided against removal of the cannula allows a surgeon to insert the cannula 10 under slight resistance to a predetermined depth at which the resistance will reduce. The cannula 10 can then be retracted slightly until increased resistance is felt, providing direct tactile feedback to indicate that the cannula is correctly placed in the artery. The increased resistance provided against removal also prevents accidental or unintentional withdrawal of the cannula 10 from the artery. This is important because if the second aperture 18 moves outside the artery, blood may flow from the cannula outside the artery causing bleeding.

By providing a protuberance in the form of a rounded shoulder, ridges, rails or barbs which can create channels for bleeding during insertion and removal are avoided.

The rearward portion of the protuberance 20 is disposed at a predetermined distance from the second aperture 18 so that when the cannula 10 is placed in a desired position in an artery, the second aperture 18 is positioned well within the artery.

The rearward portion of the protuberance 20 lies against the arteriotomy to act as a scaffold, effectively stenting open the downstream artery, which would otherwise move to conform with the shape of the cannula and compress the downstream artery potentially occlude flow from a side perfusion hole down the artery. By stenting open the artery, the protuberance maintains a channel through which blood can flow unobstructed down the leg.

Figure 3:
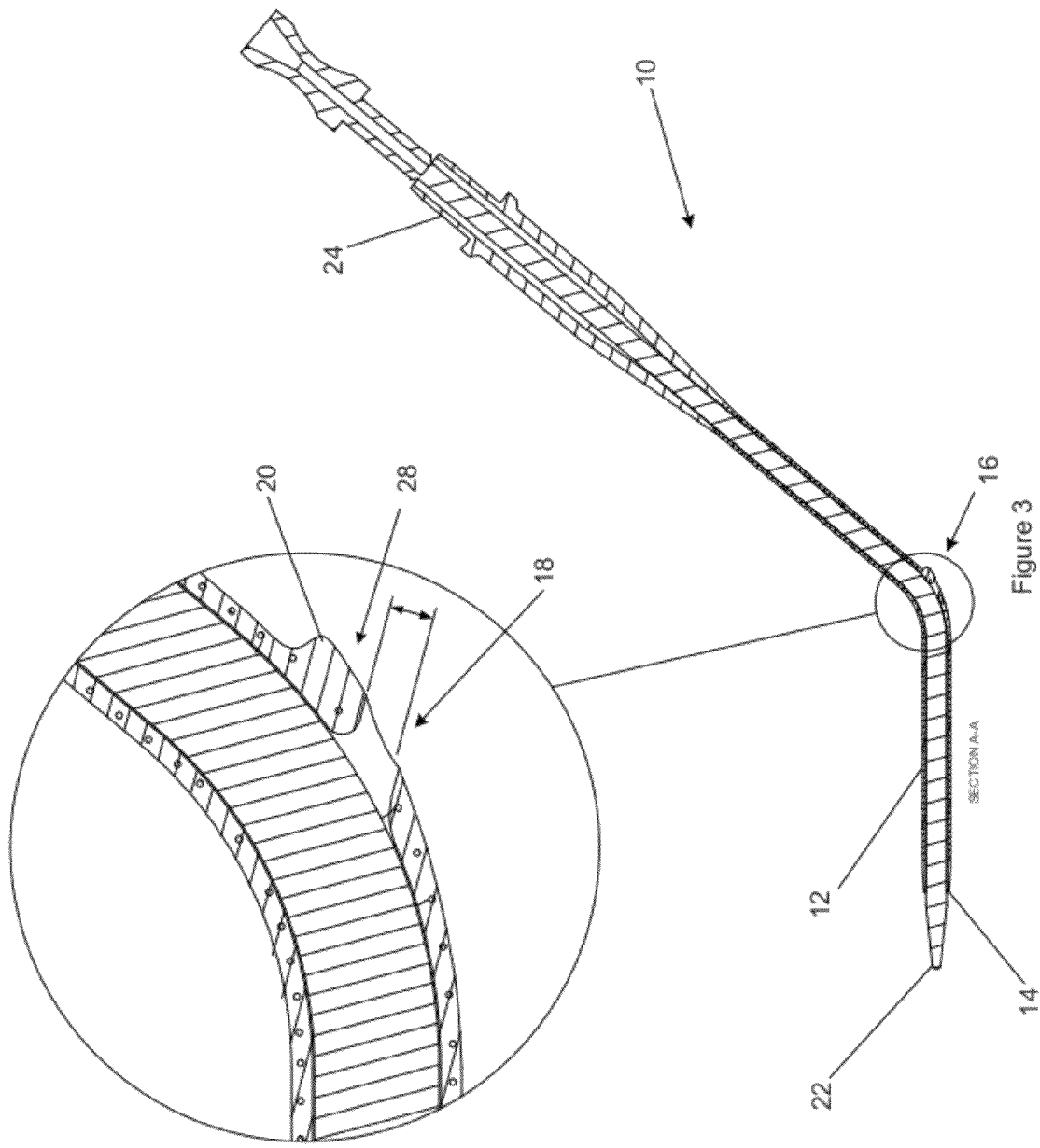
FIG. 3 is a sectional view of the cannula along line A-A of FIG. 4.

In the examples shown, the second aperture 18 extends through the protuberance 20 and in a direction generally away from the forward end of the tube, as can be seen in FIG. 3, so as to provide flow to a lower limb which is generally unimpeded. Due to the size of the cannula and the artery into which it is intended to be received, the protuberance generally surrounds the second aperture 18 so that the second aperture 18 is well placed within the artery when the cannula is positioned within the artery.

As can be seen in FIG. 2, an innermost portion of the second aperture 18 which is inside the lumen of the elongate tube 12 is generally funnel shaped to minimise turbulence of blood flowing within the elongate tube 12 and through the second aperture 18. The size of the second aperture 18 may be varied in accordance with differently sized elongate tubes to achieve different proportions of flow to the lower limb. In the example shown, the diameter of the second aperture 18 is 2.0 mm.

As can be seen in FIG. 2, the elongate tube 12 terminates at the first aperture 14. It can also be seen that the elongate tube 12 tapers at the forward end in a region proximal the first aperture 14. A flexible elongate introducer 22 can be received through the elongate tube 12 with its tip passing out of the first aperture 14. The introducer 22 aids insertion into the artery by providing a tapered end protruding out of the first aperture 14. The introducer also prevents blood flowing back from the first aperture 14. The first aperture 14 is configured to engage the introducer 22 which is received through the elongate tube 12 to prevent blood flow through the first aperture 14 and into the elongate tube 12 whilst an introducer 22 is received in the elongate tube 12.

As can be seen in FIG. 7, the elongate tube 12 can be configured so that an internal diameter of the elongate tube 12, in a region around the second aperture 18, is greater than a diameter of a corresponding portion of the elongate introducer 22 when received therethrough so that blood can pass into the elongate tube 12 through the second aperture 18 to indicate that the second aperture 18 has passed into the artery 21. In this regard, the elongate introducer 22, when inserted in the elongate tube, narrows in the region of the second aperture 18 to allow entry of blood into the elongate tube 12. The internal diameter of the elongate tube 12 is generally constant along a length of the elongate tube 12.

The resulting flash of blood entering the elongate tube 12 as the second aperture 18 passes into the artery provides a physician with a visual indication that the cannula 10 is almost in position. This flash of blood is particularly helpful during percutaneous insertion. Inserting the cannula 10 a little further into the artery 21 from this position allows a rearward portion of the protuberance 20 to pass into the artery. Once this rearward portion has passed into the artery 21, the sharper taper of the rearward portion of the protuberance 20 works to prevent accidental or unintentional withdrawal.

As can be seen in FIG. 6A, forward of the protuberance 20 and rearward of the taper proximal the first aperture 14, the external diameter of the elongate tube 12 is generally constant before transitioning into the protuberance 20 (FIG. 6B). The diameter of the elongate tube 12 transitions back or returns to this constant value rearward of the protuberance 20, as can be seen in FIG. 6C. The size of the elongate tube 12 is selected to provide adequate blood flow to the patient and an external diameter of the elongate tube may be between approximately 3 mm and approximately 8 mm. Depending on the size of the patient and the elongate tube used, obstruction of flow around the body of the cannula may occur.

The elongate tube 12 is formed of flexible material so as to at least partially straighten out when an introducer 22 is inserted into the cannula 10 to facilitate insertion of the cannula 10 into an artery. Once the introducer 22 is removed, the elongate tube 12 will return to its natural shape so as to splint open the artery, as discussed above. The elongate tube 12 may become almost completely straight when an introducer 22 is inserted into the cannula 10. As can be seen in FIG. 2, the elongate tube 12 is formed of a wire-reinforced material. In the described example, the elongate tube is formed of a flexible polyurethane material which is generally transparent, though it will be appreciated that other materials, such as silicone may also be used.

In some examples, different sections of the cannula 10 may be made from different materials. For example, the elbow 16 may be formed from a different material than the elongate tube 12. Furthermore, the elbow 16 may be formed of a flexible material such as PVC, polyurethane, silicone or rubber and configured so as to be inflatable. An inflatable elbow may be configured for manual inflation or configured to be self inflating. In such an example, the elbow 16 may remain in an uninflated or partially inflated state during insertion then become inflated to a form generally in accordance with that previously described ready for use. In this regard, when in position and inflated, the inflatable elbow provides a protuberance 20 and houses the second aperture 18 so that bi-directional perfusion can be achieved. The inflatable elbow may be configured to expand against the inner wall of the artery to hold the cannula in place and to keep the wall spaced from the second aperture 18.

A proximal end 24 of the cannula 10 is shown with a standard ⅜" connector. Such a generic fitting may be used, or other commercially available fittings may be substituted to allow the cannula 10 to be used with different perfusion tubing.

The previously described embodiments have been described in relation to generally inserting the cannula 10 into an artery. It will be appreciated that the cannula 10 is suitable for direct insertion into the artery with open surgical exposure and also suitable for percutaneous use.

During percutaneous use, which may continue for a number of days, it is desirable to ensure that the cannula remains correctly placed in the artery so that adequate perfusion is maintained. To ensure that adequate perfusion is maintained, the pressure of blood flowing into the artery behind the cannula and toward a limb, i.e. the perfusion blood which is flowing away from the arterial circulation of the patient, may be monitored.

Figure 8A:
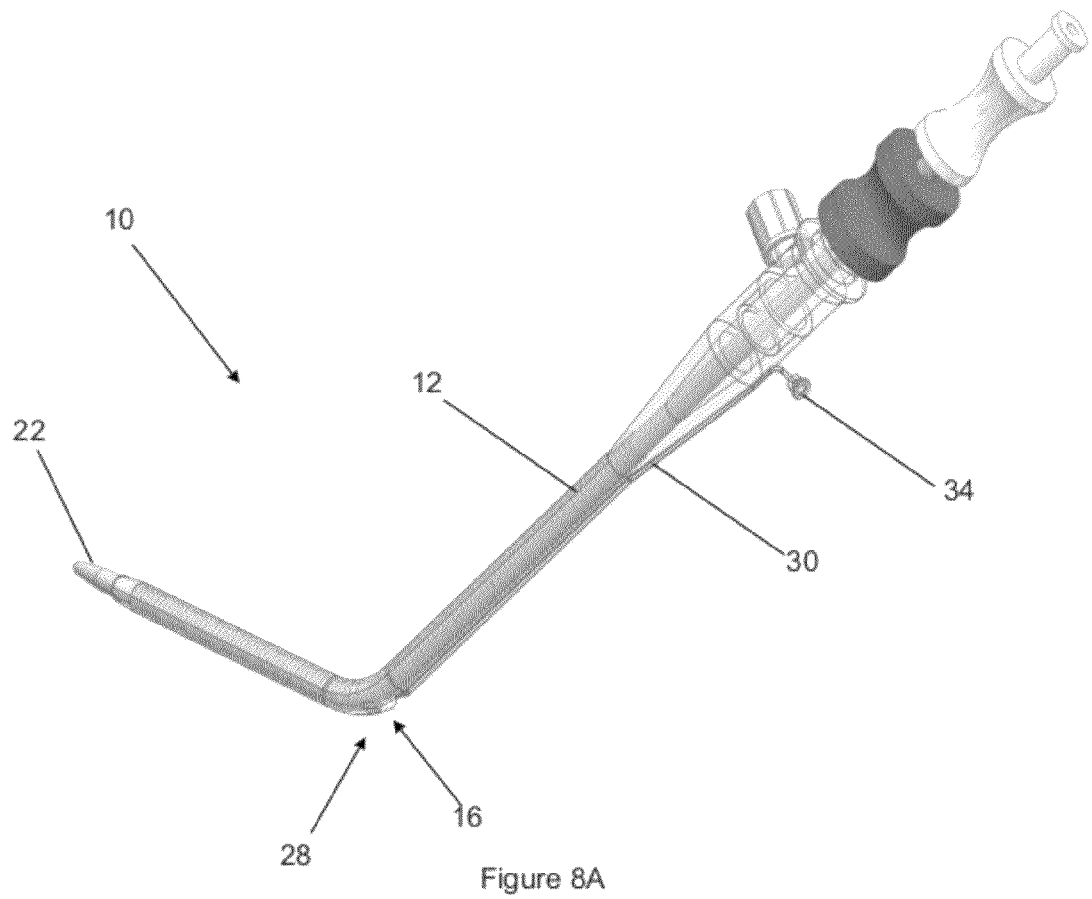
FIG. 8A is a rear perspective view of the cannula with a manometer tube affixed thereto.
Figure 8B:
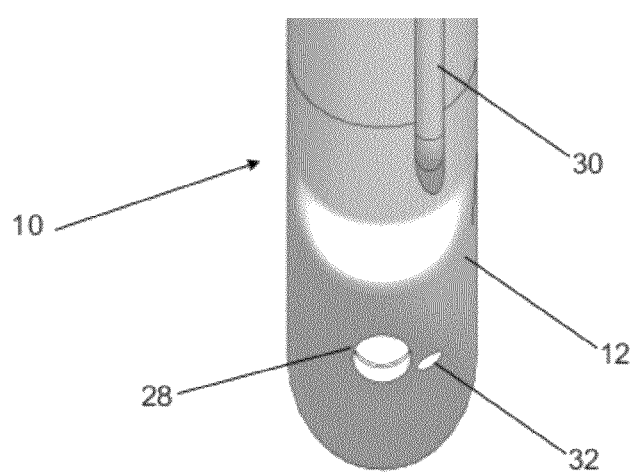
FIG. 8B is a close rear view of the manometer tube.

FIGS. 8A and 8B illustrate an example of an arrangement for monitoring a pressure of perfusion blood flowing toward a limb, so as to indicate adequacy of downstream flow and position of the cannula 10. In the illustrated example, a manometer tube 30 extends adjacent to the elongate tube 12. The manometer tube 30 passes through a wall of the elongate tube at a location behind the protuberance 20 in the insertion direction. This location is such that its position will be outside the patient in use. It will be appreciated that the manometer tube 30 may pass through the wall of the elongate tube at other locations behind the protuberance 20 and still provide the required communication between the manometer tube 30 and a pressure transducer. The manometer tube 30 passes through the elongate tube 12 and terminates at aperture 32 which is adjacent the second aperture 18. The position of the aperture 32 is such that the pressure of blood flowing toward the limb may be monitored.

The manometer tube 30 is configured to accept a connector 34 to allow connection between the manometer tube 30 and a pressure transducer (not shown). In use, when the cannula 10 is inserted in the artery, blood will flow through the aperture 18 and into an artery of the patient toward a limb. The pressure transducer will measure the pressure of this blood flowing toward the limb so that it may be determined if there is sufficient flow toward the limb. A reading from the pressure transducer may thus be used to indicate if the cannula is placed correctly in the artery. In this regard, when the cannula is placed correctly in the artery, the pressure reading will initially demonstrate pulsatile flow transmitted through the elongate tube from aperture 14. Once non-pulsatile flow commences through the elongate tube, monitoring the trend in pressure as well as the absolute pressure, will indicate any changes in perfusion towards the limb. Incorrect placement may involve the cannula being inserted too far into the artery, in which case the second aperture may become covered, or not being inserted far enough, in which case the second aperture would not be located within the artery and there would be little or no flow into the artery.

The pressure transducer may also be used to confirm that an initial placement of the cannula 10 is correct.

The use of a pressure transducer may be beneficial in environments where prolonged perfusion is common, such as Extra Corporeal Membrane Oxygenation (ECMO) units and in Intensive Care Units.

To allow insertion of the cannula 10 and tapered introducer 22 into an artery, known guide wire techniques are used.

A method of inserting the bi-directional perfusion cannula 10 into an artery comprises the steps of feeding the distal end of the elongate tube 12 with introducer 22 received therethrough into the artery (over a guide wire after predilating the artery with dilators) until an increase in resistance to insertion is felt to indicate that the protuberance 20 is entering the artery. The elongate tube 12 is then eased into the artery until the elbow 16 and the protuberance 20 have passed into the artery and the amount of resistance reduces. The elongate tube 12 is then retracted until an increase in resistance to retraction is felt to indicate that the protuberance 20 is abutting the artery wall and the cannula 10 is in position.

Once the cannula is in position, the introducer 22 may be removed so that the cannula 10 can be connected to suitable perfusion equipment.

After treatment, the cannula 10 is retracted by easing the protuberance 20 through a wall of the artery, whereby an opening formed in the artery wall is gradually enlarged by the increasing cross sectional size of the protuberance 20 so that the elongate tube 12 can be removed generally without causing further trauma to the artery. Pressure may be applied to the femoral artery at a distal location to assist in passing of the protuberance through the artery wall so that the elongate tube can be withdrawn.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A bi-directional perfusion cannula comprising an elongate tube configured for insertion into an artery, the elongate tube comprising:
   a distal portion comprising a generally cylindrical shape extending along a first longitudinal axis, a generally circular cross-section having a substantially uniform wall thickness, and a first aperture operable to direct blood flow from the tube in a first direction;
   a proximal portion comprising a generally cylindrical shape extending along a second longitudinal axis that is not collinear with the first longitudinal axis, and a generally circular cross-section having a substantially uniform wall thickness; and
   an intermediate portion extending between the distal portion and the proximal portion comprising:
     a generally arcuate shape;
     a generally oval cross-section comprising a substantially non-uniform wall thickness, a portion of the wall having a greater wall thickness and comprising a shoulder tapering outwardly in the direction toward the proximal portion;
     a passageway comprising a substantially unobstructed flow path through the intermediate portion; and
     a second aperture comprising an opening from the passageway through the portion of the wall having a greater wall thickness that is operable to direct blood flow from the tube in a second direction that is generally opposite to the first direction.

2. The cannula of claim 1 wherein the first longitudinal axis and the second longitudinal axis form an angle of about 90° to about 150°.

3. The cannula of claim 2 wherein the first longitudinal axis and the second longitudinal axis form an angle of about 130°.

4. The cannula of claim 1 wherein the opening comprises a funnel-shape tapering from a larger diameter adjacent to the passageway to a smaller diameter extending through the wall.

5. The cannula of claim 1 wherein the opening extends along a third longitudinal axis that forms an acute angle with the blood flow through the tube as the blood flow approaches the opening.

6. The cannula of claim 1 wherein the intermediate portion retains the generally arcuate shape when the cannula is in a relaxed state.

7. The cannula of claim 1 wherein the shoulder facilitates the positioning of the cannula within the artery into which the cannula is inserted.

8. The cannula of claim 7 wherein the shoulder stents open a downstream side of the artery at the point where the cannula is inserted.

9. The cannula of claim 8 wherein the shoulder comprises a length that approximates the distance between the interior walls of the artery into which the cannula is inserted.

10. The cannula of claim 1 wherein the passageway comprises a generally circular cross-section having a substantially constant inner diameter.

11. The cannula of claim 1 wherein the cannula is configured to be inserted into a femoral artery.

12. The cannula of claim 1 wherein the elongate tube is configured to receive an elongate introducer therethrough to aid in the insertion of the cannula into the artery and to prevent blood flow through the first aperture while the elongate tube and introducer are being inserted into the artery.

13. The cannula of claim 1 further comprising a tapered introducer received through the elongate tube.

14. The cannula of claim 1 further comprising a manometer tube in communication with a pressure transducer, the manometer tube configured for measuring the pressure of blood flow from the tube in the second direction.

15. The cannula of claim 1 wherein the intermediate portion is formed from one of PVC, polyurethane, silicone and rubber.

16. A bi-directional perfusion cannula configured for insertion into an artery, the cannula comprising:
    a distal portion extending along a first longitudinal axis and comprising a first aperture located at a distal end operable to direct blood flow from the cannula in an insertion direction;
    a proximal portion extending along a second longitudinal axis, wherein the first longitudinal axis and the second longitudinal axis are not collinear;
    an intermediate portion located between the distal portion and the proximal portion, the intermediate portion comprising:
      means for alleviating compression of the artery into which the cannula is inserted in a portion of the artery located downstream of the point of insertion of the cannula;
      means for stenting open the artery into which the cannula is inserted at a downstream side of the point of insertion of the cannula;
      means for directing blood flow from the cannula in a downstream direction; and
      wherein the means for directing blood flow from the cannula in a downstream direction comprises:
        a passageway comprising an unobstructed flow path; and
        a cross-section having a substantially non-uniform wall thickness, wherein a portion of the wall having a greater wall thickness comprises an opening from the passageway through the wall.

17. The cannula of claim 16 wherein the means for alleviating downstream compression of the artery comprises an elbow portion in the cannula, wherein when the cannula is in a relaxed state, the elbow portion creates an angle between the distal portion and the proximal portion of about 90° to about 150°.

18. The cannula of claim 16 wherein the means for stenting open the artery comprises a cross-section having a substantially non-uniform wall thickness, wherein a portion of the wall having a greater wall thickness comprises an outwardly tapering shoulder having a length that approximates the distance between the interior walls of the artery.

19. The cannula of claim 16, wherein the passageway comprises a generally circular cross-section having a substantially constant inner diameter.

20. The cannula of claim 16 wherein the cannula is configured to be inserted into a femoral artery.

\* \* \* \* \*